US010150099B2

(12) United States Patent
Hagemeyer et al.

(10) Patent No.: US 10,150,099 B2
(45) Date of Patent: *Dec. 11, 2018

(54) ZIRCONIUM OXIDE-DOPED CATALYST SUPPORT, METHOD FOR PRODUCING THE SAME AND CATALYST CONTAINING A ZIRCONIUM OXIDE-DOPED CATALYST SUPPORT

(76) Inventors: Alfred Hagemeyer, Bad Aibling (DE); Gerhard Mestl, München (DE); Peter Scheck, Gilching (DE)

( * ) Notice: Subject to any disclaimer, the term of this patent is extended or adjusted under 35 U.S.C. 154(b) by 323 days.

This patent is subject to a terminal disclaimer.

(21) Appl. No.: 12/601,420

(22) PCT Filed: May 30, 2008

(86) PCT No.: PCT/EP2008/004335
§ 371 (c)(1),
(2), (4) Date: Oct. 18, 2012

(87) PCT Pub. No.: WO2008/145394
PCT Pub. Date: Dec. 4, 2008

(65) Prior Publication Data
US 2010/0185010 A1    Jul. 22, 2010

(30) Foreign Application Priority Data
May 31, 2007  (DE) .......................... 10 2007 025 223

(51) Int. Cl.
| *C07C 67/05* | (2006.01) |
| *B01J 21/06* | (2006.01) |
| *B01J 21/16* | (2006.01) |
| *B01J 23/66* | (2006.01) |
| *B01J 35/08* | (2006.01) |
| *B01J 37/02* | (2006.01) |
| *B01J 37/04* | (2006.01) |
| *C07C 67/055* | (2006.01) |
| *B01J 23/10* | (2006.01) |
| *B01J 35/00* | (2006.01) |
| *B01J 35/10* | (2006.01) |
| *B01J 37/00* | (2006.01) |
| *B01J 37/16* | (2006.01) |
| *B01J 37/28* | (2006.01) |

(52) U.S. Cl.
CPC .............. *B01J 21/16* (2013.01); *B01J 23/66* (2013.01); *B01J 35/002* (2013.01); *B01J 35/08* (2013.01); *B01J 37/0221* (2013.01); *B01J 37/0242* (2013.01); *B01J 37/0248* (2013.01); *B01J 37/04* (2013.01); *C07C 67/055* (2013.01); *B01J 21/06* (2013.01); *B01J 21/066* (2013.01); *B01J 23/10* (2013.01); *B01J 35/0006* (2013.01); *B01J 35/008* (2013.01); *B01J 35/1019* (2013.01); *B01J 35/1038* (2013.01); *B01J 35/1061* (2013.01); *B01J 37/0036* (2013.01); *B01J 37/16* (2013.01); *B01J 37/28* (2013.01); *Y02P 20/582* (2015.11)

(58) Field of Classification Search
CPC ... B01J 21/06; B01J 21/16; B01J 23/10; B01J 23/66; B01J 35/008
USPC ................... 502/161, 227, 241, 242; 560/261
See application file for complete search history.

(56) References Cited

U.S. PATENT DOCUMENTS

| 2,656,323 A | 10/1953 | Bielawski et al. |
| 3,252,757 A | 5/1966 | Granquist |
| 3,259,589 A | 7/1966 | Michalko |
| 3,565,919 A | 2/1971 | Friedrichsen et al. |
| 3,617,489 A | 11/1971 | Csicsery |
| 3,962,135 A | 6/1976 | Alafandi |
| 4,155,730 A | 5/1979 | Biberbach et al. |
| 4,407,733 A | 10/1983 | Birkenstock et al. |
| 4,409,410 A | 10/1983 | Cosyns et al. |
| 4,521,618 A | 6/1985 | Arntz et al. |
| 4,621,072 A | 11/1986 | Arntz et al. |
| 4,844,790 A | 7/1989 | Occelli |
| 4,970,804 A | 11/1990 | Hüttlin |
| 4,977,126 A | 12/1990 | Mauldin et al. |
| 4,990,266 A | 2/1991 | Vorlop et al. |
| 5,015,453 A | 5/1991 | Chapman |
| 5,066,365 A | 11/1991 | Roscher et al. |
| 5,145,650 A | 9/1992 | Hüttlin |
| 5,175,136 A | 12/1992 | Felthouse |
| 5,179,056 A | 1/1993 | Bartley |
| 5,189,123 A | 2/1993 | Gropper et al. |
| 5,213,771 A | 5/1993 | Hilliard et al. |
| 5,248,644 A | 9/1993 | Johnson |
| 5,250,487 A * | 10/1993 | Wirtz et al. ................... 502/243 |
| 5,304,525 A | 4/1994 | Immel et al. |
| 5,369,069 A | 11/1994 | Suzuki |
| 5,422,329 A | 6/1995 | Wirtz et al. |
| 5,559,071 A | 9/1996 | Abel et al. |

(Continued)

FOREIGN PATENT DOCUMENTS

| CA | 1267880 | 4/1990 |
| CA | 1267882 | 4/1990 |

(Continued)

OTHER PUBLICATIONS

Figueroa (Hyperfine Study on Sol-gel Derived-Hematite Doped zirconia, Chem. Mater., 2005, 17:3486-3491).*

(Continued)

*Primary Examiner* — Jun Li

(57) ABSTRACT

The present invention relates to a porous catalyst support, consisting of a material comprising a natural sheet silicate, containing $ZrO_2$ dispersed throughout the material. The present invention also relates to a method for the production of the catalyst support according to the invention and to a shell catalyst containing the catalyst support according to the invention and also the use of the catalyst according to the invention in particular for the production of vinyl acetate monomer (VAM).

20 Claims, No Drawings

(56) References Cited

U.S. PATENT DOCUMENTS

| | | |
|---|---|---|
| 5,567,839 A | 10/1996 | Gulliver et al. |
| 5,571,771 A | 11/1996 | Abel et al. |
| 5,591,688 A | 1/1997 | Blum et al. |
| 5,622,908 A | 4/1997 | Abel et al. |
| 5,648,576 A | 7/1997 | Nguyen Than et al. |
| 5,650,371 A * | 7/1997 | Culross .......... 502/305 |
| 5,665,667 A | 9/1997 | Lemanski et al. |
| 5,668,074 A | 9/1997 | Wu et al. |
| 5,700,753 A | 12/1997 | Wang et al. |
| 5,753,583 A | 5/1998 | Heineke et al. |
| 5,801,285 A | 9/1998 | Waldmann et al. |
| 5,808,136 A | 9/1998 | Tacke et al. |
| 5,888,472 A | 3/1999 | Bem et al. |
| 5,935,889 A | 8/1999 | Murrell et al. |
| 5,990,344 A | 11/1999 | Couves et al. |
| 6,015,769 A | 1/2000 | Wang |
| 6,017,847 A | 1/2000 | Wang |
| 6,074,979 A | 6/2000 | Hagemeyer et al. |
| 6,090,746 A | 7/2000 | Bünnemann et al. |
| 6,156,927 A | 12/2000 | Halcom et al. |
| 6,207,610 B1 | 3/2001 | Krause et al. |
| 6,228,800 B1 | 5/2001 | Yamaguchi et al. |
| 6,268,522 B1 | 7/2001 | Hagemeyer et al. |
| 6,288,295 B1 | 9/2001 | Didillon et al. |
| 6,313,063 B1 | 11/2001 | Rytter et al. |
| 6,316,383 B1 | 11/2001 | Tacke et al. |
| 6,350,717 B1 | 2/2002 | Frenzel et al. |
| 6,350,900 B1 | 2/2002 | Wang et al. |
| 6,358,882 B1 | 3/2002 | Salem et al. |
| 6,367,165 B1 | 4/2002 | Hüttlin |
| 6,395,676 B2 | 5/2002 | Blum et al. |
| 6,399,813 B1 | 6/2002 | Blum et al. |
| 6,420,308 B1 | 7/2002 | Khanmamedova |
| 6,486,093 B2 | 11/2002 | Wang et al. |
| 6,492,299 B1 | 12/2002 | Couves et al. |
| 6,528,453 B2 | 3/2003 | Baker et al. |
| 6,528,683 B1 | 3/2003 | Heidemann et al. |
| 6,534,438 B1 | 3/2003 | Baker et al. |
| 6,534,672 B2 | 3/2003 | Salem et al. |
| 6,593,270 B1 | 7/2003 | Krause et al. |
| 6,603,038 B1 | 8/2003 | Hagemeyer et al. |
| 6,605,739 B1 | 8/2003 | Karim et al. |
| 6,734,131 B2 | 5/2004 | Shih et al. |
| 6,797,669 B2 | 9/2004 | Zhang et al. |
| 6,806,382 B2 | 10/2004 | Baker et al. |
| 6,821,922 B1 | 11/2004 | Tacke et al. |
| 6,849,243 B1 | 2/2005 | Hagemeyer et al. |
| 6,898,869 B2 | 5/2005 | Hüttlin |
| 6,949,141 B2 | 9/2005 | Hüttlin |
| 6,987,200 B2 | 1/2006 | Hagemeyer et al. |
| 6,992,040 B2 | 1/2006 | Müller et al. |
| 7,288,686 B2 | 10/2007 | Ryu |
| 7,468,455 B2 | 12/2008 | Mazanec et al. |
| 7,569,508 B2 | 8/2009 | Zhou et al. |
| 7,797,854 B2 | 9/2010 | Huettlin |
| 8,207,327 B2 | 6/2012 | Laar et al. |
| 8,927,452 B2 | 1/2015 | Hagemeyer et al. |
| 9,617,187 B2 | 4/2017 | Hagemeyer et al. |
| 2001/0018401 A1 | 8/2001 | Blum et al. |
| 2001/0048970 A1 | 12/2001 | Hagemeyer et al. |
| 2002/0028966 A1 | 3/2002 | Blum et al. |
| 2002/0032349 A1* | 3/2002 | Baker .................. B01J 35/0006 564/423 |
| 2002/0052290 A1 | 5/2002 | Bowman et al. |
| 2002/0062039 A1 | 5/2002 | Salem et al. |
| 2003/0003035 A1* | 1/2003 | Stamires et al. ............. 422/225 |
| 2003/0036476 A1 | 2/2003 | Arnold et al. |
| 2003/0047586 A1* | 3/2003 | Shibasaki et al. ............. 228/101 |
| 2003/0144544 A1 | 7/2003 | Baker et al. |
| 2003/0187293 A1 | 10/2003 | Birke et al. |
| 2003/0187294 A1 | 10/2003 | Hagemeyer et al. |
| 2003/0195114 A1 | 10/2003 | Tacke et al. |
| 2003/0233012 A1 | 12/2003 | Jackson et al. |
| 2004/0048937 A1 | 3/2004 | Srinivasan et al. |
| 2004/0235650 A1 | 11/2004 | Saleh et al. |
| 2005/0034322 A1 | 2/2005 | Hüttlin |
| 2005/0181940 A1 | 8/2005 | Wang et al. |
| 2005/0203320 A1 | 9/2005 | Ryu |
| 2006/0035780 A1 | 2/2006 | Xu |
| 2006/0135809 A1* | 6/2006 | Kimmich et al. ............. 560/241 |
| 2006/0266673 A1 | 11/2006 | Rende et al. |
| 2007/0041795 A1 | 2/2007 | Neto et al. |
| 2007/0135302 A1 | 6/2007 | Neto et al. |
| 2007/0191651 A1 | 8/2007 | Coupard et al. |
| 2007/0234586 A1 | 10/2007 | Huettlin |
| 2008/0287290 A1 | 11/2008 | Wang et al. |
| 2009/0305882 A1 | 12/2009 | Dahar |
| 2010/0140181 A1 | 6/2010 | Tastayre |
| 2010/0185010 A1 | 7/2010 | Hagemeyer |
| 2010/0197956 A1 | 8/2010 | Hagemeyer et al. |
| 2010/0217052 A1 | 8/2010 | Ungar et al. |
| 2010/0222209 A1 | 9/2010 | Kashani-Shirazi |
| 2010/0261603 A1 | 10/2010 | Hagemeyer et al. |
| 2011/0017289 A1 | 1/2011 | Park |
| 2011/0166010 A1 | 7/2011 | Hagemeyer et al. |
| 2012/0279556 A1 | 11/2012 | Choi |

FOREIGN PATENT DOCUMENTS

| | | |
|---|---|---|
| CA | 1268018 | 4/1990 |
| CA | 1268165 | 4/1990 |
| CA | 2 338 961 A1 | 2/2000 |
| CA | 2612435 | 12/2006 |
| CN | 1929916 | 3/2007 |
| DE | 1 286 021 B1 | 1/1969 |
| DE | 27 03 801 A1 | 8/1978 |
| DE | 28 48 978 A1 | 5/1980 |
| DE | 29 45 913 A1 | 6/1981 |
| DE | 31 19 850 A1 | 2/1982 |
| DE | 261 104 A5 | 10/1988 |
| DE | 40 06 935 A1 | 9/1991 |
| DE | 40 39 026 A1 | 6/1992 |
| DE | 44 05 876 A1 | 10/1995 |
| DE | 44 43 705 A1 | 6/1996 |
| DE | 195 34 493 A1 | 3/1997 |
| DE | 195 38 799 A1 | 4/1997 |
| DE | 196 01 861 A1 | 7/1997 |
| DE | 197 34 974 A1 | 2/1999 |
| DE | 197 34 975 A1 | 3/1999 |
| DE | 198 34 569 A1 | 2/2000 |
| DE | 199 04 147 A1 | 8/2000 |
| DE | 199 14 066 A1 | 10/2000 |
| DE | 100 64 084 A1 | 7/2002 |
| DE | 697 11 320 T2 | 7/2002 |
| DE | 102 48 116 B3 | 4/2004 |
| DE | 602 06 752 T2 | 7/2006 |
| DE | 20 2005 003 791 U1 | 8/2006 |
| DE | 10 2005 029 200 A1 | 12/2006 |
| DE | 102007025223 | 12/2008 |
| DE | 102007025443 | 12/2008 |
| EP | 0 064 301 A1 | 11/1982 |
| EP | 0262962 | 4/1988 |
| EP | 0 370 167 A1 | 5/1990 |
| EP | 0 436 787 A1 | 7/1991 |
| EP | 0 565 952 A1 | 3/1993 |
| EP | 0 634 208 A1 | 7/1994 |
| EP | 0 723 810 A1 | 7/1996 |
| EP | 0 839 793 A1 | 5/1998 |
| EP | 0 839 797 A1 | 5/1998 |
| EP | 0 882 507 A1 | 12/1998 |
| EP | 0 899 013 A1 | 3/1999 |
| EP | 1 102 635 | 2/2000 |
| EP | 1 323 469 A2 | 7/2003 |
| EP | 0 634 209 A1 | 7/2004 |
| EP | 0 634 214 A1 | 7/2004 |
| EP | 1 452 230 A1 | 9/2004 |
| EP | 1 979 073 | 7/2007 |
| GB | 585571 | 2/1947 |
| GB | 1 258 371 | 1/1970 |
| GB | 1 229 749 A1 | 4/1971 |
| GB | 1 283 737 | 8/1972 |
| JP | 0648724 | 2/1994 |
| JP | 2003-527962 | 9/2003 |
| JP | 2005246197 | 9/2005 |

(56) References Cited

FOREIGN PATENT DOCUMENTS

| | | |
|---|---|---|
| JP | 2006-239588 | 9/2006 |
| JP | 2006-255600 | 9/2006 |
| JP | 2007-506540 | 3/2007 |
| JP | 2011501691 | 1/2011 |
| KR | 19960000019 | 1/1996 |
| KR | 1020060103514 | 10/2006 |
| KR | 1020110047714 | 5/2011 |
| WO | WO 98/14274 A1 | 4/1998 |
| WO | WO 98/18553 A1 | 5/1998 |
| WO | WO 98/37102 A1 | 8/1998 |
| WO | WO 99/22860 A1 | 5/1999 |
| WO | WO 99/62632 A1 | 12/1999 |
| WO | WO 00/58008 A1 | 10/2000 |
| WO | WO 02/100527 A1 | 12/2002 |
| WO | WO 2005/061107 A1 | 7/2005 |
| WO | WO 2005/065821 A1 | 7/2005 |
| WO | WO 2006/027009 A1 | 3/2006 |
| WO | WO 2006/045606 A1 | 5/2006 |
| WO | WO 2006/078926 A1 | 7/2006 |
| WO | WO 2008/107050 A1 | 9/2008 |

OTHER PUBLICATIONS

International Search Report, Dated Nov. 13, 2008.
Elliott P. Barrett et al., "The Determination of Pore Volume and Area Distributions in Porous Substances. I. Computations from Nitrogen Isotherms," *J. Am. Chem. Soc.*, vol. 73, 1951, pp. 373-380.
Stephen Brunauer et al., "Adsorption of Gases in Multimolecular Layers," *J. Am. Chem. Soc.*, vol. 60, 1938, pp. 309-319.
Textbook of Inorganic Chemistry, Hollermann Wiberg, de Gruyter, $102^{nd}$ Edition, 2007 (ISBN 978-3-11-017770-1), at pp. 955-959, 965-970.
Römpp Chemical Dictionary, $10^{th}$ Edition, Georg Thieme Verlag, at pp. 3427-3428, 1996.
Office Action in U.S. Appl. No. 12/601,399 dated May 9, 2012.
Response filed in U.S. Appl. No. 12/601,399 on Aug. 9, 2012.
Office Action in U.S. Appl. No. 12/601,419 dated Jan. 30, 2012.
Response filed in U.S. Appl. No. 12/601,419 on May 30, 2012.
Office Action in U.S. Appl. No. 12/601,419 dated Aug. 6, 2012.
Response filed in U.S. Appl. No. 12/601,419 on Oct. 5, 2012.
Office Action in U.S. Appl. No. 12/601,777 dated Jan. 9, 2012.
Response filed in U.S. Appl. No. 12/601,777 on May 9, 2012.
Office Action in U.S. Appl. No. 12/601,777 dated Jun. 12, 2012.
Response filed in U.S. Appl. No. 12/601,777 on Sep. 12, 2012.
Office Action in U.S. Appl. No. 12/602,315 dated Aug. 16, 2012.
Office Action in U.S. Appl. No. 12/601,900 dated Jan. 4, 2012.
Montmorillonite, Mineral Data Publishing, Version 1.2 (2001).
Office Action in U.S. Appl. No. 12/601,985 dated Feb. 7, 2013.
Kohl et al., Gas purification, $5^{th}$ Edition, Gulf Publishing Company pp. 40-73 (1997).
Komai et al., Journal of Catalysis 120, 370-376 (1989).
L.A. Boot et al., Journal of Material Science, vol. 31, 1996, pp. 3115-3121 (1996).
Lehrbuch de anorganischen Chemie, Hollemann Wiberg, de Gruyter 102, Auflage, (ISBN 978-3-11-017770-1), pp. 955-970, term Schichtsllkate (2007).
Reddy et al., Fluor's Econamine FG Plus$^{SM}$ Technology, presented at the Second National Conference on Carbon Sequestration, National Energy Technology Department of Energy, Alexandria, VA, USE, pp. 1-11, May 5-8, 2003.
Römpp Chemical Dictionary, $10^{th}$ Edition (1997), Georg Thieme Verlag, at pp. 374-375.
Usubharatana et al., Energy Procedia, vol. 1, Issue 1, pp. 95-102 (2009).
Office Action in U.S. Appl. No. 12/601,419 dated Aug. 2, 2013.
Office Action in U.S. Appl. No. 12/601,777 dated Aug. 29, 2013.
Response filed in U.S. Appl. No. 12/601,777 on Aug. 6, 2013.
Office Action in U.S. Appl. No. 12/601,985 dated Sep. 24, 2013.
Notice of Allowance in U.S. Appl. No. 12/601,419 dated Sep. 24, 2013.
IN248153, Huttlin et al., Published Jun. 24, 2011, English language equivalent of WO2006/027009.
International Preliminary Report on Patentability for PCT/EP2008/004328 dated Feb. 2, 2010.
Chinese Serach Report for Application No. 200980147978.8 dated Jun. 2013.
International Search Report of PCT/EP2008/004327 dated Jan. 28, 2009.
International Search Report of PCT/EP2008/004328 dated Oct. 16, 2008.
International Search Report of PCT/EP2008/004329 dated Feb. 27, 2009.
International Search Report of PCT/EP2009/008469 filed Nov. 27, 2009, dated Apr. 28, 2010.
Stauffer, D. et al., Introduction to Percolation Theory, 2nd Edition, Taylor and Fransis, London, 1994.
International Search Report of PCT/EP2008/004334 dated Aug. 29, 2008.
International Search Report of PCT/EP2008/004332 dated Mar. 5, 2009.
International Search Report of PCT/EP2008/004333 dated Nov. 26, 2008.

\* cited by examiner

US 10,150,099 B2

ZIRCONIUM OXIDE-DOPED CATALYST SUPPORT, METHOD FOR PRODUCING THE SAME AND CATALYST CONTAINING A ZIRCONIUM OXIDE-DOPED CATALYST SUPPORT

CROSS REFERENCE TO RELATED APPLICATIONS

This is a U.S. National Phase application of PCT application number PCT/EP2008/004335, filed May 30, 2008, which claims priority benefit of German application number DE 10 2007 025 223.6 (filed May 31, 2007), the content of such applications being incorporated herein by reference.

FIELD OF INVENTION

The present invention relates to a porous catalyst support consisting of a material comprising a natural sheet silicate.

BACKGROUND OF THE INVENTION

VAM is an important monomer building block in the synthesis of plastic polymers. The main fields of use of VAM are i.a. the preparation of polyvinyl acetate, polyvinyl alcohol and polyvinyl acetal and co- and terpolymerization with other monomers such as for example ethylene, vinyl chloride, acrylate, maleinate, fumarate and vinyl laurate.

VAM is produced predominantly in the gas phase from acetic acid and ethylene by reaction with oxygen, wherein the catalysts used for this synthesis preferably contain Pd and Au as active metals and also an alkali metal component as promoter, preferably potassium in the form of the acetate. In the Pd/Au system of these catalysts, the active metals Pd and Au are not present in the form of metal particles of the respective pure metal, but rather in the form of Pd/Au-alloy particles of possibly different composition, although the presence of unalloyed particles cannot be ruled out. As an alternative to Au, for example Cd or Ba can also be used as second active metal component.

Currently, VAM is predominantly produced by means of so-called shell catalysts in which the catalytic active metals of the catalyst do not fully penetrate the catalyst support formed as a shaped body, but rather are contained only in an outer area (shell) of greater or lesser width of the catalyst support shaped body (cf. on this EP 565 952 A1, EP 634 214 A1, EP 634 209 A1 and EP 634 208 A1), while the areas of the support lying further inside are almost free of noble metals. With the help of shell catalysts, a more selective reaction control is possible in many cases than with catalysts in which the supports are impregnated with the active components into the core of the support ("impregnated through").

The shell catalysts known in the state of the art for the production of VAM can be for example catalyst supports based on silicon oxide, aluminium oxide, aluminosilicate, titanium oxide or zirconium oxide (cf. on this EP 839 793 A1, WO 1998/018553 A1, WO 2000/058008 A1 and WO 2005/061107 A1). Catalyst supports based on titanium oxide or zirconium oxide are currently scarcely used, however, as these catalyst supports do not display long-term stability compared with acetic acid and are relatively expensive.

The great majority of the catalysts currently used for the production of VAM are shell catalysts with a Pd/Au shell on a porous amorphous aluminosilicate support formed as a sphere based on natural sheet silicates in the form of natural acid-treated calcined bentonites which are thoroughly impregnated with potassium acetate as promoter.

Such VAM shell catalysts are usually produced by the so-called chemical route in which the catalyst support is loaded with or soaked in solutions of corresponding metal precursor compounds, for example by dipping the support into the solutions, or by means of the incipient wetness method (pore-filling method) in which the support is loaded with or soaked in a volume of solution corresponding to its pore volume. The Pd/Au shell of the catalyst is produced for example by first soaking the catalyst support shaped body in a first step in an $Na_2PdCl_4$ solution and then in a second step fixing the Pd component with NaOH solution onto the catalyst support in the form of a Pd-hydroxide compound. In a subsequent, separate third step, the catalyst support is then soaked in an $NaAuCl_4$ solution and then the Au component is likewise fixed by means of NaOH. After the fixing of the noble-metal components in an outer shell of the catalyst support, the loaded catalyst support is then very largely washed free of chloride and Na ions, then dried, calcined and finally reduced with ethylene at 150° C. The thus-produced Pd/Au shell is usually approximately 100 to 500 μm thick.

Usually, the catalyst support loaded with the noble metals is loaded with potassium acetate after the fixing or reducing step, wherein, rather than the loading with potassium acetate taking place only in the outer shell loaded with noble metals, the catalyst support is completely impregnated with the promoter. A spherical support called "KA-160" from SÜD-Chemie AG based on natural acid-treated calcined bentonites as sheet silicate, which has a BET surface area of approximately 160 $m^2$/g, is predominantly used as catalyst support.

The VAM selectivities, achieved by means of the VAM shell catalysts known in the state of the art based on Pd and Au as active metals and KA-160 supports as catalyst supports, are approximately 90 mol-% relative to the supplied ethylene, wherein the remaining 10 mol-% of the reaction products are essentially $CO_2$ which is formed by total oxidation of the organic educts/products.

To increase the activity of these catalysts, the active-metal-free catalyst support shaped bodies based on natural silicates were firstly surface-doped with zirconium oxide before deposition of the noble metal. For this, for example, a finished bentonite-based shaped body was impregnated with a solution of a zirconium oxide precursor compound and the precursor compound converted into the corresponding oxide by calcining of the shaped body.

Although, compared with the corresponding catalysts with a Pd/Au shell known in the state of the art, such catalysts are characterized by an increased activity in respect of VAM production, the activity can be increased to only a limited extent, as the $ZrO_2$ coats pores in which Pd and Au of oxidation stage 0 are also to be deposited. If the support is overloaded with $ZrO_2$, a decrease in the activity of the catalyst can be observed.

SUMMARY OF THE INVENTION

An object of the present invention is therefore to provide a catalyst support by means of which VAM catalysts can be produced which are characterized by a relatively high VAM activity.

This object is achieved by a first porous catalyst support, consisting of a material comprising a natural sheet silicate, containing $ZrO_2$ is dispersed throughout in the material.

Surprisingly it was found that, by incorporating $ZrO_2$ into a material comprising a natural sheet silicate of which the matrix of the porous support is formed, catalyst supports can be obtained by means of which VAM catalysts can be produced which are characterized by a relatively high VAM activity.

In addition, VAM catalysts produced by means of the first catalyst support are characterized by a relatively high VAM selectivity and tend only slightly towards thermal aging over relatively long service lives.

The first catalyst support according to aspects of the invention is also characterized by a high chemical resistance in the VAM synthesis. While the $ZrO_2$ incorporated into the sheet silicate matrix is largely resistant to acetic acid, and the support therefore displays a higher long-term stability and accordingly a corresponding catalyst has a high activity over long service lives, with supports of the state of the art the surface-impregnated $ZrO_2$ is converted relatively quickly into zirconyl acetate, which does not act as a promoter in the VAM synthesis, and washed out.

In addition, the catalyst support according to aspects of the invention is particularly cost-favourable. The production of the catalyst support according to aspects of the invention includes only one calcining step in which for example a mixture of a pulverulent sheet silicate and a pulverulent zirconium oxide precursor compound is calcined, and is thus in this respect more cost-favourable than a surface-doping of a previously calcined support with zirconium oxide precursor compounds followed by a second calcining or the application of zirconium oxide precursor compounds as suspensions to previously calcined supports (WO2005065821) and their subsequent calcining, wherein this process actually also requires an additional binder, usually zirconyl acetate, in order to obtain an adequate strength of the catalyst support.

A VAM catalyst produced by means of the first catalyst support according to aspects of the invention is characterized by a particularly high VAM activity and selectivity if the $ZrO_2$ is uniformly dispersed, preferably homogeneously, throughout the material.

The $ZrO_2$ can be contained in the material in the form of individual $ZrO_2$ units which are integrated into the skeleton structure of the material. But it is preferred that the $ZrO_2$ is present in particulate form. A firm incorporation of the $ZrO_2$ in the material and thus a high thermal resistance to aging of a catalyst produced by means of the first catalyst support according to aspects of the invention. The $ZrO_2$ particles preferably have an average diameter of 1 nm to 100 µm, preferably an average diameter of 0.5 µm to 20 µm.

DETAILED DESCRIPTION OF THE PREFERRED EMBODIMENTS

Within the framework of the present invention, the terms "catalyst support shaped body", "catalyst support", "shaped body" and "support" are used synonymously.

An object according to aspects of the invention is further achieved by a second porous catalyst support, formed as a shaped body, with an outer shell, wherein the catalyst support, at least in the area of the outer shell, is formed from a matrix comprising a natural sheet silicate, in particular a matrix comprising an acid-treated calcined bentonite, in which zirconium oxide ($ZrO_2$) particles are dispersed uniformly, preferably homogeneously.

The second catalyst support according to aspects of the invention displays the same advantages as the first catalyst support according to aspects of the invention.

It is preferred if the whole second catalyst support is formed from a matrix comprising a natural sheet silicate in which zirconium oxide ($ZrO_2$) particles are uniformly dispersed. The $ZrO_2$ particles preferably have an average diameter of 1 nm to 100 µm, preferably an average diameter of 0.5 µm to 20 µm.

The present invention furthermore relates to a third porous catalyst support comprising a natural sheet silicate, wherein the catalyst support comprises at least 3 mass-% zirconium oxide, preferably in particulate form, wherein the $ZrO_2$ particles preferably have a diameter of 1 nm to 100 µm, preferably a diameter of 0.5 µm to 20 µm.

The preferred embodiments below relate both to the first and second and also to the third catalyst support according to aspects of the invention.

It is preferred that the zirconium oxide particles are contained in the catalyst support at a proportion of from 1 to 25 mass-%, preferably at a proportion of from 3 to 20 mass-% and by preference at a proportion of from 5 to 20 mass-% relative to the mass of the catalyst support. If the zirconium oxide is represented in the catalyst support at a proportion of less than 1 mass-%, the activity-increasing properties of the zirconium oxide have only a slight effect, while above a proportion of 25 mass-% the increase in activity of the catalyst can be accompanied by a clear decrease in VAM selectivity.

According to a preferred embodiment of the catalyst support according to aspects of the invention, its solubility in acetic acid is less than 8 wt.-%, preferably less than 4 wt.-% and particularly preferably less than 2 wt.-%. To determine acetic acid solubility, 5 g of the catalyst support are ground to powder and treated in 125 ml 96-% acetic acid (p.a.) for 1 h under reflux conditions. The catalyst support is separated off over a filter. The eluate is evaporated to dryness and the mass m (residue) of the solid residue determined and the acetic acid solubility calculated as follows: acetic acid solubility=(m(residue)/5 g)*100%.

Low solubility values of the catalyst support according to aspects of the invention can be obtained by treating the catalyst support with acid after its production.

Accordingly, according to a further preferred embodiment, the catalyst support is a support treated with an acid.

It is further preferred if the catalyst support displays an acidity of between 1 and 150 µval/g, preferably between 5 and 130 µval/g, quite preferably between 10 and 100 µval/g and particularly preferably between 10 and 60 µval/g.

The acidity of the catalyst support can advantageously influence the activity of the catalyst according to aspects of the invention during the gas phase synthesis of VAM from acetic acid and ethene. The acidity of the catalyst support is determined as follows: 100 ml water (with a pH blank value) is added to 1 g of the finely ground catalyst support and extraction is carried out for 15 minutes accompanied by stirring. Titration to at least pH 7.0 with 0.01 n NaOH solution follows, wherein the titration is carried out in stages; 1 ml of the NaOH solution is firstly added dropwise to the extract (1 drop/second), followed by a 2-minute wait, the pH is read, a further 1 ml NaOH added dropwise, etc. The blank value of the water used is determined and the acidity calculation corrected accordingly.

The titration curve (ml 0.01 NaOH against pH) is then plotted and the intersection point of the titration curve determined at pH 7. The mole equivalents which result from the NaOH consumption for the intersection point at pH 7 are calculated in $10^{-6}$ equiv/g support.

$$\text{Total acid:} \frac{10 * \text{ml } 0.01 \text{ n NaOH}}{1 \text{ support}} = \mu\text{val/g}$$

In addition, it is preferred that the catalyst support has an average pore diameter of from 8 to 30 nm, from preferably 9 to 20 nm and by preference from 10 to 15 nm.

It was found that, the smaller the surface of the catalyst support according to aspects of the invention, the higher the VAM selectivity of the catalyst according to aspects of the invention. By "surface" of the catalyst support is meant within the framework of the present invention the BET surface area of the support, which is determined by means of adsorption of nitrogen according to DIN 66132.

Therefore it can be preferred that the catalyst support has a BET surface area less than/equal to 145 m$^2$/g, preferably less than/equal to 142 m$^2$/g, by preference less than/equal to 140 m$^2$/g, further preferably less than/equal to 137 m$^2$/g, more preferably less than/equal to 135 m$^2$/g, still more preferably less than/equal to 133 m$^2$/g and particularly preferably less than/equal to 130 m$^2$/g.

It is further preferred according to aspects of the invention that the catalyst support has a BET surface area of from 60 to 145 m$^2$/g, preferably between 65 and 140 m$^2$/g, preferably between 70 and 135 m$^2$/g, further preferably between 70 and 120 m$^2$/g, more preferably between 70 and 110 m$^2$/g and most preferably between 70 and 100 m$^2$/g.

It is also preferred that the catalyst support has a hardness greater than/equal to 20 N, preferably greater than/equal to 25 N, further preferably greater than/equal to 35 N and most preferably greater than/equal to 40 N. The hardness (indentation hardness) is to be determined as stated below.

By "natural sheet silicate", for which "phyllosilicate" is also used in the literature, is meant within the framework of the present invention untreated or treated silicate material from natural sources, in which SiO$_4$ tetrahedra, which form the structural base unit of all silicates, are cross-linked with each other in layers of the general formula [Si$_2$O$_5$]$^{2-}$. These tetrahedron layers alternate with so-called octahedron layers in which a cation, principally Al and Mg, is octahedrally surrounded by OH or O. A distinction is drawn for example between two-layer phyllosilicates and three-layer phyllosilicates. Sheet silicates preferred within the framework of the present invention are clay minerals, in particular kaolinite, beidellite, hectorite, saponite, nontronite, mica, vermiculite and smectites, wherein smectites and in particular montmorillonite are particularly preferred. Definitions of "sheet silicates" are to be found for example in "Lehrbuch der anorganischen Chemie", Hollemann Wiberg, de Gruyter, 102$^{nd}$ edition, 2007 (ISBN 978-3-11-017770-1) or in "Römpp Lexikon Chemie", 10$^{th}$ edition, Georg Thieme Verlag under "phyllosilicate". Typical treatments to which a natural sheet silicate is subjected before use as support material include for example a treatment with acids and/or calcining. A natural sheet silicate particularly preferred within the framework of the present invention is a bentonite. Admittedly, bentonites are not really natural sheet silicates, more a mixture of predominantly clay minerals containing sheet silicates. Thus in the present case, where the natural sheet silicate is a bentonite, it is to be understood that the natural sheet silicate is present in the catalyst support in the form of or as a constituent of a bentonite. It is particularly preferred that the bentonite is acid-treated and calcined.

It is preferred that the proportion of natural sheet silicate in the catalyst support is greater than/equal to 50 mass-%, preferably greater than/equal to 60 mass-%, preferably greater than/equal to 70 mass-%, further preferably greater than/equal to 80 mass-%, more preferably greater than/equal to 90 mass-% and most preferably greater than/equal to 93 mass-%, relative to the mass of the catalyst support.

It was found that the VAM selectivity of a VAM catalyst depends on the integral pore volume of the catalyst support according to aspects of the invention. It is therefore preferred that the catalyst support has an integral BJH pore volume of between 0.25 and 0.7 ml/g, preferably between 0.3 and 0.55 ml/g and by preference 0.35 to 0.5 ml/g.

The integral pore volume of the catalyst support is determined according to the BJH method by means of nitrogen adsorption. The surface of the catalyst support and its integral pore volume are determined according to the BET or according to the BJH method. The BET surface area is determined according to the BET method according to DIN 66131; a publication of the BET method is also found in J. Am. Chem. Soc. 60, 309 (1938). In order to determine the surface and the integral pore volume of the catalyst support or the catalyst, the sample can be measured for example with a fully automatic nitrogen porosimeter from Micromeritics, type ASAP 2010, by means of which an adsorption and desorption isotherm is recorded.

To determine the surface and the porosity of the catalyst support according to the BET theory, the data are evaluated according to DIN 66131. The pore volume is determined from the measurement data using the BJH method (E. P. Barret, L. G. Joiner, P. P. Haienda, J. Am. Chem. Soc. 73 (1951, 373)). Effects of capillary condensation are also taken into account when using this method. Pore volumes of specific pore size ranges are determined by totalling incremental pore volumes which are obtained from the evaluation of the adsorption isotherms according to BJH. The integral pore volume according to the BJH method relates to pores with a diameter of 1.7 to 300 nm.

It is preferred according to a further preferred embodiment of the catalyst support according to aspects of the invention if at least 80%, preferably at least 85% and by preference at least 90%, of the integral pore volume of the catalyst support is formed by mesopores and macropores. This counteracts a reduced activity, effected by diffusion limitation, of the catalyst according to aspects of the invention, in particular with relatively thick Pd/Au shells. By "micropores", "mesopores" and "macropores" are meant in this case pores which have a diameter of less than 2 nm, a diameter of 2 to 50 nm and a diameter of greater than 50 nm respectively.

It is also preferred if the catalyst support has a bulk density of more than 0.3 g/ml, preferably more than 0.35 g/ml and particularly preferably a bulk density of between 0.35 and 0.6 g/ml.

It is further preferred if the natural sheet silicate contained in the support has an SiO$_2$ content of at least 65 mass-%, preferably at least 80 mass-% and by preference 95 to 99.5 mass-%. An adequate chemical resistance of the catalyst support according to aspects of the invention is thereby ensured.

In the gas-phase synthesis of VAM from acetic acid and ethene, a relatively low Al$_2$O$_3$ content in the natural sheet silicate is scarcely disadvantageous, whereas with high Al$_2$O$_3$ contents a marked reduction in indentation hardness must be expected. According to a preferred embodiment of the catalyst support according to aspects of the invention, the natural sheet silicate therefore contains less than 10 mass-% Al$_2$O$_3$, preferably 0.1 to 3 mass-% and by preference 0.3 to 1.0 mass-%, relative to the mass of the natural sheet silicate.

It is preferred according to a further preferred embodiment of the catalyst support according to aspects of the invention that the catalyst support is formed as a shaped body, for example as a sphere, cylinder, perforated cylinder, trilobe, ring, star or as a strand, preferably as ribbed strand or star-shaped strand, preferably as sphere.

In addition, it is preferred that the catalyst support is formed as a sphere with a diameter greater than 2 mm, preferably with a diameter greater than 3 mm and by preference with a diameter greater than 4 mm.

In addition, it is preferred that the maximum size of the catalyst support is smaller than 25 mm, preferably smaller than 10 mm.

It can also be preferred, in order to increase the activity of a VAM catalyst, that the catalyst support according to aspects of the invention is doped with at least one oxide of a metal, selected from the group consisting of Hf, Ti, Nb, Ta, W, Mg, Re, Y and Fe, preferably with $HfO_2$ or $Fe_2O_3$. It is further preferred in this connection that the proportion of doping oxide in the catalyst support is between 0 and 20 mass-%, preferably 1.0 to 10 mass-% and by preference 3 to 8 mass-%. The doping can take place for example by surface doping, as is known from the state of the art, or the metal oxide/metal oxides can be incorporated into the matrix of the catalyst support, like the $ZrO_2$ of the catalyst support according to aspects of the invention.

In the catalyst support according to aspects of the invention, the zirconium oxide particles are preferably present in the form of microcrystallites and/or nanocrystallites, wherein the zirconium oxide is not necessarily present therein as pure $ZrO_2$, as it can also be present in the form of a mixed oxide.

It can be preferred that the $ZrO_2$ particles themselves are doped with $Y_2O_3$ or $HfO_2$.

It can be provided according to a further preferred embodiment that the water absorbency of the catalyst support is 40 to 75%, preferably 50 to 70% calculated as the weight increase due to water absorption. The absorbency is determined by soaking 10 g of the support sample in deionized water for 30 min until gas bubbles no longer escape from the support sample. The excess water is then decanted and the soaked sample blotted with a cotton towel to remove adhering moisture from the sample. The water-laden support is then weighed and the absorbency calculated as follows:

(amount weighed out (g)−amount weighed in (g))×
10=water absorbency (%)

The present invention also relates to a method for the production of a catalyst support, in particular a catalyst support according to aspects of the invention.

The catalyst support according to aspects of the invention can be produced for example by grinding a pulverulent (uncalcined) acid-treated bentonite as sheet silicate with a pulverulent zirconium compound and water and then mixing thoroughly until homogeneous, shaping the resulting mixture, accompanied by compaction, into a shaped body by means of devices familiar to a person skilled in the art, such as for example extruders or tablet presses, and then calcining the unhardened shaped body to form a stable shaped body. The calcining is carried out at temperatures at which a solid structure is obtained and optionally the zirconium compound is converted into zirconium oxide $ZrO_2$. The size of the specific surface area (BET) of the catalyst support depends in particular on the quality of the (untreated) bentonite used, the acid-treatment method of the bentonite used, i.e. for example the nature and the quantity, relative to the bentonite, and the concentration of the inorganic acid used, the acid-treatment duration and temperature, on the moulding pressure and on the calcining duration and temperature and the calcining atmosphere.

Acid-treated bentonites can be obtained by treating bentonites with strong acids such as for example sulphuric acid, phosphoric acid or hydrochloric acid. A definition, also valid within the framework of the present invention, of the term bentonite is given in Römpp, Lexikon Chemie, 10$^{th}$ edition, Georg Thieme Verlag. Bentonites particularly preferred within the framework of the present invention are natural aluminium-containing sheet silicates which contain montmorillonite (as smectite) as main mineral. After the acid treatment, the bentonite is as a rule washed with water, dried and ground to a powder.

The method according to aspects of the invention for the production of a catalyst support, in particular a catalyst support according to aspects of the invention, comprises the steps:
a) mixing a pulverulent natural sheet silicate, in particular a pulverulent acid-treated bentonite, with pulverulent zirconium metal or a pulverulent zirconium compound;
b) calcining the obtained mixture.

The production of a catalyst support according to the method according to aspects of the invention thus has only a single calcining step and is thus in this respect more cost-favourable than a surface-doping of a previously calcined support with zirconium oxide precursor compounds followed by a second calcining, or the application of zirconium dioxide or zirconium oxide precursor compounds as suspensions to previously calcined supports (WO2005065821) and their subsequent calcining, wherein this method actually also requires an additional binder, usually zirconyl acetate, in order to obtain an adequate strength of the catalyst support.

The calcining is preferably carried out at a temperature of 400° C. to 800° C., preferably at a temperature of 500° C. to 700° C.

According to a preferred embodiment of the method according to aspects of the invention, the latter further comprises the step: shaping a shaped body from the obtained mixture, preferably before carrying out step b).

The zirconium compound, provided it is not already zirconium oxide, is preferably converted into an oxide during the calcining.

The above-named method results in catalyst supports with a solid structure of sheet silicate and zirconium oxide particles sintered together, wherein the zirconium oxide particles are uniformly dispersed in the structure of the particles.

In the above-named method, zirconium dioxide, zirconium hydroxide, zirconyl acetate or other zirconyl carboxylates, zirconium carbonate or zirconium oxycarbonate, zirconyl nitrate, zirconium naphthenate or ammonium zirconium carbonate, preferably zirconium hydroxide, are preferably used as pulverulent zirconium compound. Where $ZrO_2$ is used, it can be stabilized with $Y_2O_3$ and/or $HfO_2$. A sintering of the constituents of the matrix of the catalyst support shaped body to form a stable structure of sheet silicate and optionally zirconium oxide particles is thereby guaranteed.

According to a further preferred embodiment of the method according to aspects of the invention, the method further comprises the step: treating the calcined mixture with an acid. A low acetic-acid solubility of the support when used in VAM synthesis is thereby achieved As an alternative to a pulverulent zirconium compound, colloidal $ZrO_2$ in a solution or a corresponding sol can also be used.

According to a preferred embodiment of the method according to aspects of the invention, it is provided that the zirconium compound is converted into an oxide upon calcining.

According to a further preferred embodiment of the method according to aspects of the invention, it is preferred that zirconium oxide and/or zirconium hydroxide is used as zirconium compound.

It can also be provided that in step a) $Y_2O_3$ and/or $HfO_2$ is furthermore used.

The present invention also relates to a catalyst support which can be obtained according to the method according to aspects of the invention.

The present invention further relates to the use of the first, second and third catalyst support according to aspects of the invention in the production of a catalyst, in particular in the production of a shell catalyst.

According to a preferred embodiment of the use according to aspects of the invention, it is provided that the shell catalyst is a shell catalyst for the production of vinyl acetate monomer, in particular a shell catalyst whose shell contains metallic Pd and Au.

The present invention further relates to a shell catalyst for the production of VAM, comprising the first, second or third catalyst support according to aspects of the invention, whose shell contains metallic Pd and Au.

Thus the present invention relates i.a. to a shell catalyst for the production of VAM, comprising a porous catalyst support shaped body with an outer shell which contains metallic Pd and Au, wherein the catalyst support shaped body, at least in the area of the outer shell, is formed of a matrix comprising a natural sheet silicate, in particular a matrix comprising an acid-treated, calcined bentonite, in which zirconium oxide ($ZrO_2$) particles are uniformly, preferably homogeneously, dispersed.

It was established that the advantages of the shell catalyst according to aspects of the invention, such as increased activity and selectivity, are already obtained if only the outer shell of the catalyst support, in which the noble metals Pd and Au are deposited, is formed of a matrix comprising a natural sheet silicate, in which zirconium oxide ($ZrO_2$) particles are uniformly dispersed. However, it is preferred according to aspects of the invention if the whole catalyst support of the catalyst according to aspects of the invention is formed from a matrix comprising a natural sheet silicate, in which zirconium oxide ($ZrO_2$) particles are uniformly dispersed.

According to a preferred embodiment of the catalyst according to aspects of the invention, it is provided that the zirconium oxide particles are contained in the catalyst support at a proportion of 1 to 25 mass-%, preferably at a proportion of 3 to 20 mass-% and by preference at a proportion of 5 to 20 mass-%, relative to the mass of the catalyst support.

According to a further preferred embodiment of the catalyst according to aspects of the invention, it is provided that the catalyst support has an acidity of between 1 and 150 μval/g, preferably between 5 and 130 μval/g, quite preferably between 10 and 100 μval/g and particularly preferably between 10 and 60 μval/g.

According to a further preferred embodiment of the catalyst according to aspects of the invention, it is provided that the catalyst support has an average pore diameter of from 8 to 30 nm, preferably from 9 to 20 nm and by preference from 10 to 15 nm.

According to a further preferred embodiment of the catalyst according to aspects of the invention, it is provided that the catalyst support has a surface of less than/equal to 145 $m^2/g$, preferably less than 142 $m^2/g$, preferably less than 140 $m^2/g$, further preferably less than 137 $m^2/g$, more preferably less than 135 $m^2/g$, still more preferably less than 133 $m^2/g$ and particularly preferably less than 130 $m^2/g$.

According to a preferred embodiment of the catalyst according to aspects of the invention, it is provided that the catalyst support has a surface of from 60 $m^2/g$ to 145 $m^2/g$, preferably between 65 $m^2/g$ and 140 $m^2/g$, by preference between 70 $m^2/g$ and 130 $m^2/g$, further preferably between 70 $m^2/g$ and 120 $m^2/g$, more preferably between 70 $m^2/g$ and 110 $m^2/g$ and most preferably between 70 $m^2/g$ and 100 $m^2/g$.

In particular to keep the wear of the catalyst according to aspects of the invention within reasonable limits, the catalyst has a hardness greater than/equal to 20 N, preferably greater than/equal to 25 N, further preferably greater than/equal to 35 N and most preferably greater than/equal to 40 N. The hardness is ascertained by means of an 8M tablet-hardness testing machine from Dr. Schleuniger Pharmatron AG, determining the average for 99 shell catalysts after drying of the catalyst at 130° C. for 2 h, wherein the apparatus settings are as follows:

Hardness: N
Distance from the shaped body: 5.00 mm
Time delay: 0.80 s
Feed type: 6 D
Speed: 0.60 mm/s The hardness of the catalyst can be influenced for example by varying certain parameters of the method for the production of the catalyst support, for example through the selection of the natural sheet silicate, the calcining duration and/or the calcining temperature of an unhardened shaped body shaped from the corresponding support mixture, or through specific additives such as for example methyl cellulose or magnesium stearate.

According to a further preferred embodiment of the catalyst according to aspects of the invention, it is provided that the proportion of natural sheet silicate, in particular acid-treated calcined bentonite, in the catalyst support is greater than/equal to 50 mass-%, preferably greater than/equal to 60 mass-%, preferably greater than/equal to 70 mass-%, further preferably greater than/equal to 80 mass-%, more preferably greater than/equal to 90 mass-% and most preferably greater than/equal to 93 mass-%, relative to the mass of the catalyst support.

According to a further preferred embodiment of the catalyst according to aspects of the invention, it is provided that the catalyst support has an integral BJH pore volume of between 0.25 and 0.7 ml/g, preferably between 0.3 and 0.55 ml/g and by preference between 0.35 and 0.5 ml/g.

According to a further preferred embodiment of the catalyst support according to aspects of the invention, it is provided that at least 80%, preferably at least 85% and by preference at least 90%, of the integral pore volume of the catalyst support is formed by mesopores and macropores.

According to a further preferred embodiment of the catalyst according to aspects of the invention, it is provided that the catalyst support has a bulk density of more than 0.3 g/ml, preferably more than 0.35 g/ml and particularly preferably a bulk density of between 0.35 and 0.6 g/ml.

According to a further preferred embodiment of the catalyst according to aspects of the invention, it is provided that the natural sheet silicate contained in the support has an $SiO_2$ content of at least 65 mass-%, preferably at least 80 mass-% and by preference from 95 to 99.5 mass-%.

According to a further preferred embodiment of the catalyst according to aspects of the invention, it is provided that the natural sheet silicate contained in the support contains less than 10 mass-% $Al_2O_3$, preferably 0.1 to 3 mass-% and by preference 0.3 to 1.0 mass-%.

According to a further preferred embodiment of the catalyst support according to aspects of the invention, it is provided that the catalyst support is formed as a shaped body, preferably as a sphere, cylinder, perforated cylinder, trilobe, ring, star or as a strand, preferably as a ribbed strand or star-shaped strand, preferably as a sphere.

According to a further preferred embodiment of the catalyst according to aspects of the invention, it is provided that the catalyst support is formed as a sphere with a diameter greater than 2 mm, preferably with a diameter greater than 3 mm and by preference with a diameter greater than 4 mm.

In addition, it is preferred that the maximum size of the catalyst support is less than 25 mm, preferably less than 10 mm.

According to a further preferred embodiment of the catalyst according to aspects of the invention, it is provided that the catalyst support is doped with at least one oxide of a metal, selected from the group consisting of Hf, Ti, Nb, Ta, W, Mg, Re, Y and Fe, preferably with $HfO_2$ or $Fe_2O_3$.

According to a further preferred embodiment of the catalyst according to aspects of the invention, it is preferred that the proportion of doping oxide in the catalyst support is between 0 and 20 mass-%, preferably 1.0 to 10 mass-% and by preference 3 to 8 mass-%.

In general, the smaller the thickness of the Pd/Au shell of the catalyst, the higher the VAM selectivity of the catalyst according to aspects of the invention. According to a further preferred embodiment of the catalyst according to aspects of the invention, the shell of the catalyst therefore has a thickness of less than/equal to 300 μm, preferably of less than/equal to 200 μm, preferably of less than/equal to 150 μm, further preferably of less than/equal to 100 μm and more preferably of less than/equal to 80 μm.

The thickness of the shell can be measured visually by means of a microscope. The area in which the noble metals are deposited appears black, while the areas free of noble metals appear white. As a rule, the boundary between areas containing noble metals and areas free of them is very sharp and can clearly be recognized visually. If the above-named boundary is not sharply defined and accordingly not clearly recognizable visually, the thickness of the shell corresponds to the thickness of a shell, measured starting from the outer surface of the catalyst support, which contains 95% of the noble metal deposited on the support.

It was likewise found that in the case of the catalyst according to aspects of the invention the Pd/Au shell can be formed with a relatively large thickness effecting a high activity of the catalyst, without effecting a noteworthy reduction of the VAM selectivity of the catalyst according to aspects of the invention. According to another preferred embodiment of the catalyst according to aspects of the invention, the shell of the catalyst therefore has a thickness of between 200 and 2000 μm, preferably between 250 and 1800 μm, by preference between 300 and 1500 μm and further preferably between 400 and 1200 μm.

In order to guarantee an adequate activity of the catalyst according to aspects of the invention, the proportion of Pd in the catalyst is 0.5 to 2.5 mass-%, preferably 0.6 to 2.3 mass-% and by preference 0.7 to 2 mass-%, relative to the mass of the catalyst support loaded with noble metal.

It can also be preferred if the catalyst according to aspects of the invention has a Pd content of 1 to 20 g/l, preferably 2 to 15 g/l and by preference 3 to 10 g/l.

In order to likewise guarantee an adequate activity and selectivity of the catalyst according to aspects of the invention, the Au/Pd atomic ratio of the catalyst is preferably between 0 and 1.2, preferably between 0.1 and 1, by preference between 0.3 and 0.9 and particularly preferably between 0.4 and 0.8.

It can also be preferred if the catalyst according to aspects of the invention has an Au content of 1 to 20 g/l, preferably 1.5 to 15 g/l and by preference 2 to 10 g/l.

In order to ensure a largely uniform activity of the catalyst according to aspects of the invention over the thickness of the Pd/Au shell, the noble-metal concentration should vary relatively little over the shell thickness. It is therefore preferred if, over an area of 90% of the shell thickness, the area being at a distance of 5% of the shell thickness from each of the outer and inner shell limit, the profile of the noble-metal concentration of the catalyst varies from the average noble-metal concentration of this area by a maximum of +/−20%, preferably by a maximum of +/−15% and by preference by a maximum of +/−10%. Such profiles can be obtained by the spraying, described below, of supports onto a fluid bed.

Chloride poisons the catalyst according to aspects of the invention and leads to a deactivation of same. According to a further preferred embodiment of the catalyst according to the invention, its chloride content is therefore less than/equal to 250 ppm, preferably less than/equal to 150 ppm.

The catalyst according to aspects of the invention preferably contains, in addition to zirconium oxide as further promoter, at least one alkali metal compound, preferably a potassium, sodium, caesium or rubidium compound, preferably a potassium compound. Suitable and particularly preferred potassium compounds include potassium acetate KOAc, potassium carbonate $K_2CO_3$, potassium hydrogen carbonate $KHCO_3$ and potassium hydroxide KOH and also all potassium compounds which change into K-acetate KOAc under the respective reaction conditions of VAM synthesis. The potassium compound can be deposited on the catalyst support both before and after the reduction of the metal components into the metals Pd and Au. According to a further preferred embodiment of the catalyst according to aspects of the invention, the catalyst comprises an alkali metal acetate, preferably potassium acetate. It is particularly preferred in order to ensure an adequate promoter activity if the alkali metal acetate content of the catalyst is 0.1 to 0.7 mol/l, preferably 0.3 to 0.5 mol/l. In the case of potassium acetate, the potassium acetate content of the catalyst according to aspects of the invention is preferably approximately 40 g/l.

According to a further preferred embodiment of the catalyst according to aspects of the invention, the alkali metal/Pd atomic ratio is between 1 and 12, preferably between 2 and 10 and particularly preferably between 4 and 9. Preferably, the smaller the surface of the catalyst support, the smaller the alkali metal/Pd atomic ratio.

The present invention also relates to a first method for the production of a catalyst, in particular a shell catalyst, comprising the steps:

a) producing the first, second or third catalyst support according to aspects of the invention;

b) depositing a solution of a Pd precursor compound onto the catalyst support;

c) depositing a solution of an Au precursor compound onto the catalyst support;

d) converting the Pd component of the Pd precursor compound into the metallic form; and
e) converting the Au component of the Au precursor compound into the metallic form.

The outer $ZrO_2$-doped shell of the catalyst support according to aspects of the invention has a thickness which corresponds at least to the thickness of the noble-metal shell to be deposited, for example a thickness of 500 µm.

In principle, any Pd or Au compound by means of which a high degree of dispersion of the metals can be achieved can be used as Pd and Au precursor compound. By "degree of dispersion" is meant the ratio of the number of all the surface metal atoms of all metal/alloy particles of a supported metal catalyst to the total number of all the metal atoms of the metal/alloy particles. In general it is preferred if the degree of dispersion corresponds to a relatively high numerical value, as in this case as many metal atoms as possible are freely accessible for a catalytic reaction. This means that, given a relatively high degree of dispersion of a supported metal catalyst, a specific catalytic activity of same can be achieved with a relatively small quantity of metal used. According to a further preferred embodiment of the catalyst according to aspects of the invention, the degree of dispersion of the metal particles is 1 to 30%. The values of the degree of dispersion are determined by means of CO adsorption according to the corresponding DIN standard.

It can be preferred to select the Pd and Au precursor compounds from the halides, in particular chlorides, oxides, nitrates, nitrites, formates, propionates, oxalates, acetates, hydroxides, hydrogen carbonates, amine complexes or organic complexes, for example triphenylphosphine complexes or acetylacetonate complexes, of these metals.

Examples of preferred Pd precursor compounds are water-soluble Pd salts. According to a particularly preferred embodiment of the method according to aspects of the invention, the Pd precursor compound is selected from the group consisting of $Pd(NH_3)_4(OH)_2$, $Pd(NH_3)_4(OAc)_2$, $H_2PdCl_4$, $Pd(NH_3)_4(HCO_3)_2$, $Pd(NH_3)_4(HPO_4)$, $Pd(NH_3)_4Cl_2$, $Pd(NH_3)_4$ oxalate, Pd oxalate, $Pd(NO_3)_2$, $Pd(NH_3)_4(NO_3)_2$, $K_2Pd(OAc)_2(OH)_2$, $Na_2Pd(OAc)_2(OH)_2$, $Pd(NH_3)_2(NO_2)_2$, $K_2Pd(NO_2)_4$, $Na_2Pd(NO_2)_4$, $Pd(OAc)_2$, $K_2PdCl_4$, $(NH_4)_2PdCl_4$, $PdCl_2$ and $Na_2PdCl_4$. Instead of $NH_3$ the corresponding complex salts can also be used with ethylenediamine or ethanolamine as ligand. In addition to $Pd(OAc)_2$ other carboxylates of palladium can also be used, preferably the salts of the aliphatic monocarboxylic acids with 3 to 5 carbon atoms, for example the propionate or butyrate salt.

According to a further preferred embodiment of the method according to aspects of the invention, Pd nitrite precursor compounds can also be preferred. Preferred Pd nitrite precursor compounds are for example those which are obtained by dissolving $Pd(OAc)_2$ in an $NaNO_2$ solution.

Examples of preferred Au precursor compounds are water-soluble Au salts. According to a particularly preferred embodiment of the method according to aspects of the invention, the Au precursor compound is selected from the group consisting of $KAuO_2$, $HAuCl_4$, $KAu(NO_2)_4$, $AuCl_3$, $KAuCl_4$, $NaAuCl_4$, $KAuCl_4$, $KAu(OAc)_3(OH)$, $HAu(NO_3)_4$, $NaAuO_2$, $NMe_4AuO_2$, $RbAuO_2$, $CsAuO_2$, $NaAu(OAc)_3(OH)$, $RbAu(OAc)_3OH$, $CsAu(OAc)_3OH$, $NMe_4Au(OAc)_3OH$ and $Au(OAc)_3$. It is recommended where appropriate to prepare fresh $Au(OAc)_3$ or $KAuO_2$ each time by precipitating the oxide/hydroxide from a gold (III) hydroxide solution, washing and isolating the precipitate and taking up same in acetic acid or KOH.

All pure solvents or solvent mixtures in which the selected precursor compounds are soluble and which, after deposition onto the catalyst support, can be easily removed again from same by means of drying are suitable as solvents for the precursor compounds. Preferred solvents for metal acetates as precursor compounds are for example acetone or unsubstituted carboxylic acids, in particular acetic acid, and for the metal chlorides above all water or dilute hydrochloric acid.

If the precursor compounds are not sufficiently soluble in pure solvents such as acetone, acetic acid, water or dilute hydrochloric acid or mixtures thereof, other solvents or solvent additives can also be used as an alternative or in addition to the named solvents. Solvents which are inert and miscible with acetic acid or water preferably come into consideration as other solvents in this case. Ketones, for example acetone or acetylacetone, furthermore ethers, for example tetrahydrofuran or dioxan, acetonitrile, dimethylformamide and solvents based on hydrocarbons such as for example benzene may be named as preferred solvents which are suitable for adding to acetic acid.

Ketones, for example acetone, or alcohols, for example ethanol or isopropanol or methoxyethanol, lyes, such as aqueous KOH or NaOH, or organic acids, such as acetic acid, formic acid, citric acid, tartaric acid, malic acid, glyoxylic acid, glycolic acid, oxalic acid, oxamic acid, glycine, pyruvic acid or lactic acid may be named as preferred solvents or additives which are suitable for adding to water.

If chloride compounds are used as precursor compounds, it must be ensured that the chloride ions are reduced to a tolerable residual quantity before using the catalyst produced according to the method according to invention, as chloride is a catalyst poison. For this, the catalyst support is as a rule washed with plenty of water after the fixing of the Pd and Au components of the Pd or Au precursor compound onto the catalyst support. In general, this happens either immediately after the fixing by hydroxide precipitation of the Pd and Au component by means of lye or after the reduction of the noble-metal components to the respective metal/alloy.

However, according to a preferred embodiment of the method according to aspects of the invention, chloride-free Pd and Au precursor compounds are used as well as chloride-free solvents to keep the chloride content in the catalyst as low as possible and avoid a laborious "washing free of chloride". The corresponding acetate, hydroxide or nitrite compounds are preferably used as precursor compounds, as they contaminate the catalyst support with chloride to only a very small extent.

The deposition of the Pd and Au precursor compounds on the catalyst support in the area of an outer shell of the catalyst support can be achieved according to processes known per se. Thus the precursor solutions can be deposited by soaking, by dipping the support in the precursor solutions or soaking it according to the incipient wetness method. A base, for example caustic soda solution or potash lye, is then deposited on the catalyst support, whereby the noble-metal components are precipitated onto the support in the form of hydroxides. It is also possible for example to firstly soak the support in lye and then apply the precursor compounds to the thus-pretreated support.

According to a further preferred embodiment of the method according to aspects of the invention, it is therefore provided that the Pd and Au precursor compound is deposited on the catalyst support by soaking the catalyst support in the solution of the Pd precursor compound and in the solution of the Au precursor compound or in a solution which contains both the Pd and the Au precursor compound.

According to the state of the art, the active metals Pd and Au, starting from chloride compounds in the area of a shell of the support, are applied to same by means of soaking. However, this technique has reached its limits as regards minimum shell thicknesses and maximum Au loading. The shell thickness of the corresponding known VAM catalysts is at most approx. 100 μm and it is not foreseen that even thinner shells can be obtained by means of soaking. In addition, higher Au loadings within the desired shell by means of soaking can be achieved only with difficulty, as the Au precursor compounds tend to diffuse from the shell into inner zones of the catalyst support shaped body, which results in broad Au shells, areas of which contain very little Pd.

The active metals, or, put another way, their precursor compounds, can also be deposited on the support for example by means of so-called physical processes. For this, the support according to aspects of the invention can preferably be sprayed for example with a solution of the precursor compounds, wherein the catalyst support is moved in a coating drum into which hot air is blown, with the result that the solvent quickly evaporates.

But according to a further preferred embodiment of the method according to aspects of the invention, it is provided that the solution of the Pd precursor compound and the solution of the Au precursor compound are deposited onto the catalyst support by spraying the solutions onto a fluidized bed or a fluid bed of the catalyst support, preferably by means of an aerosol of the solutions. The shell thickness can thereby be continuously adjusted and optimized, for example up to a thickness of 2 mm. But even very thin noble-metal shells with a thickness of less than 100 μm are thus possible.

It is preferred if the shaped bodies circulate elliptically or toroidally in the fluid bed. To give an idea of how the shaped bodies move in such fluid beds, it may be stated that in the case of "elliptical circulation" the catalyst support shaped bodies move in the fluid bed in a vertical plane on an elliptical path, the size of the main and secondary axis changing. In the case of "toroidal circulation" the catalyst support shaped bodies move in the fluid bed in the vertical plane on an elliptical path, the size of the main and secondary axis changing, and in the horizontal plane on an orbit, the size of the radius changing. On average, the shaped bodies move in the case of "elliptical circulation" in the vertical plane on an elliptical path, in the case of "toroidal circulation" on a toroidal path, i.e., a shaped body covers the surface of a torus helically with vertical elliptical section.

The above-named embodiment of the method according to aspects of the invention is preferably carried out by means of a fluid bed in a fluid bed unit. It is particularly preferred if the unit contains a so-called controlled air-glide layer. For one thing, the catalyst support shaped bodies are thoroughly mixed by the controlled air-glide layer, wherein they simultaneously rotate about their own axis, whereby they are dried evenly by the process air. For another, due to the consequent orbital movement, effected by the controlled air-glide layer, of the shaped bodies the catalyst support shaped bodies pass through the spray procedure (application of the precursor compounds) at a virtually constant frequency. A largely uniform shell thickness of a treated batch of shaped bodies is thereby achieved. A further result is that the noble-metal concentration varies only slightly over a large area of the shell thickness, i.e. such that the noble-metal concentration describes a rectangular function over a large area of the shell thickness, whereby a uniform activity of the resulting catalyst is guaranteed over the thickness of the Pd/Au shell.

Suitable coating drums, fluidized bed units and fluid bed units for carrying out the method according to aspects of the invention according to preferred embodiments are known in the state of the art and sold e.g. by Heinrich Brucks GmbH (Alfeld, Germany), ERWEK GmbH (Heusenstamm, Germany), Stechel (Germany), DRIAM Anlagenbau GmbH (Eriskirch, Germany), Glatt GmbH (Binzen, Germany), G.S. Divisione Verniciatura (Osteria, Italy), HOFER-Pharma Maschinen GmbH (Weil am Rhein, Germany), L. B. Bohle Maschinen+Verfahren GmbH (Enningerloh, Germany), Lödige Maschinenbau GmbH (Paderborn, Germany), Manesty (Merseyside, United Kingdom), Vector Corporation (Marion, Iowa, USA), Aeromatic-Fielder AG (Bubendorf, Switzerland), GEA Process Engineering (Hampshire, United Kingdom), Fluid Air Inc. (Aurora, Ill., USA), Heinen Systems GmbH (Varel, Germany), Hüttlin GmbH (Steinen, Germany), Umang Pharmatech Pvt. Ltd. (Marharashtra, India) and Innojet Technologies (Lörrach, Germany). Particularly preferred fluid bed equipment is sold under the name Innojet® Aircoater or Innojet® Ventilus by Innojet Technologies.

According to a further preferred embodiment of the method according to aspects of the invention, the catalyst support is heated during deposition of the solutions, for example by means of heated process air. The drying-off speed of the deposited solutions of the noble-metal precursor compounds can be determined via the degree of heating of the catalyst supports. At relatively low temperatures the drying-off speed is for example relatively low, with the result that with a corresponding quantitative deposition, greater shell thicknesses can result because of the high diffusion of the precursor compounds that is caused by the presence of solvent. At relatively high temperatures the drying-off speed is for example relatively high, with the result that a solution of the precursor compounds coming into contact with the shaped body almost immediately dries off, which is why a solution deposited on the catalyst support cannot penetrate deep into the latter. At relatively high temperatures such relatively small shell thicknesses can thus be obtained with a high noble-metal loading. For example the catalyst support can be heated to a temperature of 40 to 80° C.

In the method described in the state of the art for the production of VAM shell catalysts based on Pd and Au, commercially available solutions of the precursor compounds such as $Na_2PdCl_4$, $NaAuCl_4$ or $HAuCl_4$ solutions are customarily used. In the more recent literature, as already stated previously, chloride-free Pd or Au precursor compounds such as for example $Pd(NH_3)_4(OH)_2$, $Pd(NH_3)_2(NO_2)_2$ and $KAuO_2$ are also used. These precursor compounds react base in solution, while the standard chloride, nitrate and acetate precursor compounds react acid in solution.

To deposit the precursor compounds onto the catalyst support, preferably aqueous $Na_2PdCl_4$ and $NaAuCl_3$ solutions are customarily used. These metal-salt solutions are normally applied to the support at room temperature and the metal components then fixed with NaOH as insoluble Pd or Au hydroxides. Then the loaded support is customarily washed free of chloride with water. In particular the Au fixing has disadvantages, such as long action times of the base in order to induce the precipitation of the stable Au tetrachloro complex, incomplete precipitation and concomitant inadequate Au retention.

According to a further preferred embodiment of the method according to aspects of the invention, the method comprises the steps:

a) providing a first solution of a Pd and/or an Au precursor compound;

b) providing a second solution of a Pd and/or an Au precursor compound, wherein the first solution effects a precipitation of the noble-metal component(s) of the precursor compound(s) of the second solution and vice versa;

c) depositing the first solution and the second solution onto the catalyst support.

This embodiment of the method according to aspects of the invention uses two different precursor solutions, of which for example one contains a Pd and the other an Au precursor compound. Generally, one of the solutions preferably has a basic, and the other an acid pH. Generally, the solutions are deposited onto the catalyst supports by firstly impregnating the support with the first and then in a subsequent step with the second solution as described previously, for example by soaking. Upon deposition of the second solution the two solutions are then combined on the support, whereby the pH of the solutions changes and the Pd or Au component of the respective precursor compound is precipitated onto the support, without an auxiliary base customary in the state of the art, such as NaOH or KOH, having to be applied to the support.

The named embodiment of the method according to aspects of the invention is thus based on an impregnation of the catalyst support with the first solution of a Pd and/or Au precursor compound and the second solution of a Pd and/or Au precursor compound, wherein the two solutions are incompatible with each other, i.e., the first solution effects a precipitation of the noble-metal component(s) of the precursor compound(s) of the second solution and vice versa, with the result that in the contact zone of the two solutions both the pre-impregnated Pd/Au component(s) and the post-impregnated Pd/Au component(s) precipitate almost simultaneously and thus lead to an intimate thorough mixing of Pd/Au. Drying can optionally take place between the two impregnation steps.

Suitable aqueous solutions of Pd precursor compounds for the impregnation with incompatible solutions are listed by way of example in Table 1.

TABLE 1

| Precursor compound | Character of the solution |
| --- | --- |
| $PdCl_2$ | acid |
| $Pd(NH_3)_2(NO_2)_2$ | basic |
| $Na_2PdCl_4$ | neutral |
| $Pd(NH_3)_4(OH)_2$ | basic |
| $Pd(NO_3)_2$ | acid |
| $K_2Pd(OAc)_2(OH)_2$ | basic through dissolution of palladium acetate in KOH |

If, with regard to a premature Au reduction, $NH_3$ were to have too strong a reductive effect, the corresponding diamine complexes can also be used with ethylenediamine as ligand or the corresponding ethanol amine complexes instead of the palladium amine complexes.

Suitable aqueous solutions of Au precursor compounds for the impregnation with incompatible solutions are listed by way of example in Table 2.

TABLE 2

| Precursor compound | Character of the solution |
| --- | --- |
| $AuCl_3$ | acid |
| $KAuO_2$ | basic through dissolution of $Au(OH)_3$ in KOH |
| $NaAuCl_4$ | neutral |
| $HAuCl_4$ | acid |
| $KAu(OAc)_3(OH)$ | basic through dissolution of $Au(OAc)_3$ in KOH |
| $HAu(NO_3)_4$ | acid (stable in semi-concentrated $HNO_3$) |

Suitable combinations of incompatible solutions for the base-free precipitation of the noble-metal components are for example a $PdCl_2$ and a $KAuO_2$ solution; a $Pd(NO_3)_2$ and a $KAuO_2$ solution; a $Pd(NH_3)_4(OH)_2$ and an $AuCl_3$ or $HAuCl_4$ solution.

According to a further preferred embodiment of the method according to aspects of the invention, Pd can also be precipitated with incompatible Pd solutions and analogously Au with incompatible Au solutions, e.g. by bringing a $PdCl_2$ solution into contact with a $Pd(NH_3)_4(OH)_2$ solution or a $HAuCl_4$ with a $KAuO_2$ solution. In this way high Pd and/or Au contents can precipitate in the shell without having to use highly concentrated solutions.

According to a further embodiment of the method according to aspects of the invention, mixed solutions compatible with one another which are brought into contact with a solution incompatible with the mixed solution, can also be used for the noble-metal precipitation. An example of a mixed solution is a $PdCl_2$ and $AuCl_3$-containing solution, the noble-metal components of which can be precipitated with a $KAuO_2$ solution, or a $Pd(NH_3)_4(OH)_2$- and $KAuO_2$-containing solution, the noble-metal components of which can be precipitated with a $PdCl_2$- and $HAuCl_4$-containing solution. A further example of a mixed solution is the $HAuCl_4$ and $KAuO_2$ pairing.

The impregnation with the incompatible solutions will preferably take place by means of soaking or by means of spray impregnation, wherein the incompatible solutions are for example sprayed simultaneously by one or more double nozzle(s) or simultaneously by means of two nozzles or nozzle groups or sequentially by means of one or more nozzle(s).

Because of the rapid immobilization (fixing) of the metal components of the precursor compounds in the shell and the concomitant shortened Pd and Au diffusion, the impregnation with the incompatible solutions can lead to thinner layers than the conventional use of solutions compatible with one another. By means of the incompatible solutions, high noble-metal contents in thin shells, improved metal retention, more rapid and more complete precipitation of the noble metals, the reduction of the disruptive residual Na content of the support, the simultaneous fixing of Pd and Au in only one fixing step, and also the absence of NaOH costs and NaOH handling and an avoidance of a mechanical weakening of the support through contact with excess NaOH can be achieved.

By means of the impregnation with incompatible solutions, greater noble-metal contents can be precipitated on the catalyst support through a single fixing step, which comprises just the deposition of two incompatible solutions, than is possible with standard base (NaOH) fixing.

In particular, high Au contents with an Au/Pd atomic ratio of 0.6 and more, which is very desirable with regard to the increase in VAN selectivity, can be easily achieved by means of the principle of incompatible solutions.

According to a further preferred embodiment of the method according to aspects of the invention, it is provided that, once the Pd and/or the Au precursor compound has/have been deposited onto the catalyst supports for the fixing of the noble-metal component(s) of the precursor compound(s) onto the catalyst support, the catalyst support is subjected to a fixing step. The fixing step can comprise the treatment of the support with lye or acid, depending on whether the precursor compound is acid or basic, or a calcining of the support for converting the noble-metal component(s) into a hydroxide compound(s) or into an oxide is provided for. The fixing step can also be omitted and the noble-metal components directly reduced, e.g. by treatment with a gas phase with a reductive action, e.g. ethylene, etc., at increased temperatures of 20° C. to 200° C.

It is likewise possible to produce the catalyst according to aspects of the invention by means of a pulverulent porous support material, comprising a mixture of particles of a natural sheet silicate, in particular an acid-treated (calcined or uncalcined) bentonite, and zirconium oxide ($ZrO_2$) particles, wherein the support material is loaded with a Pd and an Au precursor compound or with Pd and Au particles. The pre-treated support material can also be coated on as a secondary support e.g. in the form of a washcoat on a suitable primary support, for example a sphere of steatite or a KA-160 support from SÜD-Chemie AG, and then processed further into a catalyst by calcining and reduction.

Accordingly the invention relates to a further method for the production of a shell catalyst, in particular a shell catalyst according to aspects of the invention, comprising the steps a) providing a pulverulent porous support material, comprising a mixture of particles of a natural sheet silicate, in particular an acid-treated calcined bentonite, and zirconium oxide ($ZrO_2$) particles, wherein the support material is loaded with a Pd and an Au precursor compound or with Pd and Au particles;

b) depositing the support material from step a) onto a primary support in the form of a shell;

c) calcining the loaded support structure from step b); and d) optionally converting the Pd and the Au component of the Pd or Au precursor compound into the metallic form.

Alternatively the named method can also be carried out by firstly depositing the noble-metal-free support material onto a support structure and only then application of the noble metals.

After loading with the precursor compounds or after fixing the noble-metal components, the support can be calcined to convert the noble-metal components into the corresponding oxides. Calcining preferably takes place at temperatures of less than 700° C., particularly preferably between 300-450° C. accompanied by the addition of air. Calcining time depends on the calcining temperature and is preferably chosen in the range from 0.5-6 hours. At a calcining temperature of approx. 400° C., the calcining time is preferably 1-2 hours. At a calcining temperature of approx. 300° C., the calcining time is preferably up to 6 hours.

The noble-metal components are further reduced before the use of the catalyst, wherein the reduction can be carried out in situ, i.e. in the process reactor, or also ex situ, i.e. in a special reduction reactor. Reduction in situ is preferably carried out with ethylene (5 vol.-%) in nitrogen at a temperature of approx. 150° C. over a period of for example 5 hours. Reduction ex situ can be carried out for example with 5 vol.-% hydrogen, for example by means of forming gas, at temperatures in the range of preferably 150-500° C., over a period of 5 hours.

Gaseous or vaporable reducing agents such as for example CO, $NH_3$, formaldehyde, methanol and hydrocarbons can likewise be used, wherein the gaseous reducing agents can also be diluted with inert gas, such as for example carbon dioxide, nitrogen or argon. An inert gas-diluted reducing agent is preferably used. Mixtures of hydrogen with nitrogen or argon, preferably with a hydrogen content between 1 vol.-% and 15 vol.-%, are preferred.

The reduction of the noble metals can also be undertaken in the liquid phase, preferably by means of the reducing agents hydrazine, K-formate, $H_2O_2$, Na-hypophosphite, Na-formate, ammonium formate, formic acid, K-hypophosphite or hypophosphoric acid.

The quantity of reducing agent is preferably chosen such that during the treatment period at least the equivalent required for complete reduction of the noble-metal components is passed over the catalyst. Preferably, however, an excess of reducing agent is passed over the catalyst in order to guarantee a rapid and complete reduction.

The reduction is preferably pressureless, i.e. at an absolute pressure of approx. 1 bar. For the production of industrial quantities of catalyst according to aspects of the invention a rotary tube oven or fluidized-bed reactor is preferably used in order to guarantee an even reduction of the catalyst.

The invention also relates to the use of the catalyst according to aspects of the invention as an oxidation catalyst, as a hydrogenation/dehydrogenation catalyst, as a catalyst in the hydrogenating desulphurization, as a hydrodenitrification catalyst, as a hydrodeoxygenation catalyst or as a catalyst in the synthesis of alkenylalkanoates, in particular in the synthesis of vinyl acetate monomer (VAM), in particular in the gas-phase oxidation of ethylene and acetic acid to vinyl acetate monomer.

The catalyst according to aspects of the invention is preferably used for the production of VAM. Generally this takes place by passing acetic acid, ethylene and oxygen or oxygen-containing gases over the catalyst according to aspects of the invention at temperatures of 100-200° C., preferably 120-200° C., and at pressures of 1-25 bar, preferably 1-20 bar, wherein non-reacted educts can be recycled. Expediently, the oxygen concentration is kept below 10 vol.-%. Under certain circumstances, however, a dilution with inert gases such as nitrogen or carbon dioxide is also advantageous. Carbon dioxide is particularly suitable for dilution as it is formed in small quantities in the course of VAM synthesis. The formed vinyl acetate is isolated with the help of suitable methods, which are described for example in U.S. Pat. No. 5,066,365 A.

The following embodiment examples serve, when viewed together with a comparison example, to explain the invention:

Example 1

500 g of different acid-treated dried pulverulent bentonite mixtures as sheet silicate based on natural bentonites with montmorillonite as main constituent were ground into an intimate mixture by means of a ball mill with up to 50 g $ZrO_2$ and 12 g methyl cellulose customary in the trade.

The resultant mixture was taken up with water and processed by means of a mixer into a dough from which spherical shaped bodies were prepared under pressure by means of a tablet press. For hardening, the spheres were calcined at a temperature of 600° C. over a period of 5 h. The thus-obtainable shaped bodies have the characteristics listed in Table 3:

TABLE 3

| Geometric form | Sphere |
|---|---|
| Diameter | 5 mm |
| Moisture content | <2.0 mass-% |
| Compressive strength | >35 N |
| Bulk density | 550-600 g l$^{-1}$ |
| Water absorbency | 55-70% |
| Specific surface area (BET) | 120-160 m$^2$ g$^{-1}$ |
| SiO$_2$ content | 80 to 90 mass-% |
| ZrO$_2$ content | 3.7 to 9.5 mass-% |
| Other oxides | Residual mass in mass-% |
| Loss on ignition 1000° C. | <0.4 mass-% |
| Acidity | 10 to 100 μval/g |
| BJH pore volume N$_2$ | 0.3-0.45 cm$^3$ g$^{-1}$ |

225 g of the spheres prepared as above were packed in an Innojet Technologies (Lörrach, Germany) fluid-bed device with the trade name Innojet® Aircoater and converted, by means of compressed air (6 bar) temperature-controlled at 80° C., into a fluid-bed state in which the shaped bodies circulated toroidally, i.e. moved along a vertically aligned ellipsoid path and a horizontal circular path aligned perpendicular to this.

Once the shaped bodies were temperature-controlled at approx. 75° C., 300 ml of an aqueous noble-metal mixed solution containing 7.5 g Na$_2$PdCl$_4$ (sodium tetrachloropalladate) customary in the trade and 4.6 g NaAuCl$_4$ (sodium tetrachloroaurate) customary in the trade were sprayed onto the fluid bed of the shaped bodies over a period of 40 min.

After the impregnation of the catalyst support with the noble-metal mixed solution the support spheres were sprayed with a 0.05 molar NaOH solution in the fluid-bed state under the above conditions over a period of 30 min. The NaOH was allowed to act on the shaped bodies for 16 h.

Following exposure to the action of the NaOH, the supports were washed with plenty of water in the fluid-bed device, in order to very largely remove the alkali metal and chloride introduced into the support via the noble-metal compounds and NaOH.

After washing, the shaped bodies were dried in the fluid-bed device at a temperature of 90 to 110° C.

After the shaped bodies were dried they were reduced to a Pd/Au shell catalyst with a gas mixture of ethylene (5 vol.-%) in nitrogen at a temperature of approx. 150° C. in the fluid-bed device.

The resulting shell catalyst contained approx. 1.2 mass-% Pd and had an Au/Pd atomic ratio of approx. 0.5 (determined by means of ICP (inductively coupled plasma)), a shell thickness of approx. 180 μm and a hardness of 33 N.

The noble-metal concentration of the thus-produced Pd/Au shell catalyst varied over an area of 90% of the shell thickness, the area being at a distance of 5% of the shell thickness from each of the outer and inner shell limit, from the average noble-metal concentration of this area by a maximum of +/−10%. The noble-metal distribution was determined on a LEO 430VP scanning electron microscope, equipped with an energy-dispersive spectrometer from Bruker AXS. To measure the noble-metal concentration over the shell thickness, a catalyst sphere was cut in half, stuck to an aluminium sample holder and then vapour-deposited with carbon. A nitrogen-free silicon drift detector (XFlash® 410) with an energy resolution of 125 eV for the manganese K$_{alpha}$ line was used as detector.

Example 2

65 g support, prepared according to Example 1 with downstream acid treatment with the characteristics listed in Table 4:

TABLE 4

| Geometric form | Sphere |
|---|---|
| Diameter | 5 mm |
| Moisture content | <2.0 mass-% |
| Compressive strength | 50 N |
| Bulk density | 585 g l$^{-1}$ |
| Water absorbency | 61.3% |
| Specific surface area (BET) | 158 m$^2$ g$^{-1}$ |
| SiO$_2$ content | 83.3 mass-% |
| ZrO$_2$ content | 5.2 mass-% |
| Other oxides | Residual mass in mass-% |
| Loss on ignition 1000° C. | 3.6 mass-% |
| Acidity | 30 μval/g |
| BJH pore volume N$_2$ | 0.389 cm$^3$ g$^{-1}$ | was impregnated, using the pore-filling method (incipient wetness method), in which a support is impregnated with a volume of solution corresponding to its pore volume, with 38.6 ml of an aqueous solution containing 1.568 g Na$_2$PdCl$_4$ and 0.357 g HAuCl$_4$. After the impregnation 89.14 g of a 0.35 molar NaOH solution was applied to the catalyst support and left to stand overnight at room temperature for 21 h. After decanting of the fixing solution the thus-prepared catalyst precursor was reduced with 73.65 g of a 10% NaH$_2$PO$_2$ solution for 2 h. After draining the reduction solution the catalyst was washed with distilled water for 8 h at room temperature, the water being constantly replaced (throughflow=140 rpm) to remove Cl residues. The final value of the conductivity of the wash solution was 1.4 μS.

The catalyst was then dried in the fluidized bed at 90° C. for 70 min. The dried spheres were loaded with a mixture of 27.30 g 2 molar KOAc solution and 13.59 g H$_2$O and left to stand for 1 hour at room temperature. To conclude, drying takes place for 70 min at 90° C. in the fluidized bed.

The theoretical loading of the supports with Pd is 0.8 wt.-% and 0.3 wt.-% Au; the experimental loading was 0.78 wt.-% Pd and 0.27 wt.-% Au (determined by means of ICP).

The shell thickness was 239 μm (statistical average).

6 ml of a charge of catalyst spheres from Example 2 were impacted in a fixed-bed tubular reactor at a temperature of 150° C. at 10 bar by a feed gas stream of 550 Nml/min composed of 15% HOAc, 6% O$_2$, 39% C$_2$H$_4$ in N$_2$ and the reactor output analyzed by means of gas chromatography.

The selectivity (of ethylene to VAM) is calculated according to the formula S(C$_2$H$_4$)=mole VAM/(mole VAM+mole CO$_2$/2). The resultant space-time yield is given in g VAM/l catalyst/h. The rate of oxygen conversion is calculated according to (mole O$_2$ in −mole O$_2$ out)/mole O$_2$ in.

The catalyst according to Example 2 according to aspects of the invention produced by means of the catalyst support according to aspects of the invention displays a selectivity S(C$_2$H$_4$) of 92.4% and a space-time yield (determined by means of gas chromatography) of 840 g VAM/l catalyst/h at an oxygen conversion rate of 49.5%.

Comparison Example 100 g of a bentonite-containing support from SUD-Chemie AG (Munich, Germany) with the trade name "KA-160" with the characteristics listed in Table 5:

TABLE 5

| | |
|---|---|
| Geometric form | Sphere |
| Diameter | 5 mm |
| Moisture content | <2.0 mass-% |
| Compressive strength | >60 N |
| Bulk density | 554 g l$^{-1}$ |
| Water absorbency | 62% |
| Specific surface area (BET) | 158 m$^2$ g$^{-1}$ |
| SiO$_2$ content | 93.2 mass-% |
| Al$_2$O$_3$ content | 2.2 mass-% |
| Fe$_2$O$_3$ content | 0.35 mass-% |
| TiO$_2$ content | (total) <1.5 mass-% |
| MgO content | |
| CaO content | |
| K$_2$O content | |
| Na$_2$O content | |
| Loss on ignition 1000° C. | <0.3 mass-% |
| Acidity | 53 µval/g |
| BJH pore volume N$_2$ | 0.38 cm$^3$ g$^{-1}$ | was impregnated with 62 ml of a 9.1% (relative to Zr) aqueous zirconyl nitrate solution according to the pore-filling method (incipient wetness method). The support was then dried at 120° C. over a period of 5 h and then calcined at 450° C. in air for 2 h. In this way a KA 160 support surface-doped with 5.2 wt.-% ZrO$_2$ was obtained.

Using the surface-doped KA 160 support, a catalyst was produced analogously to Example 2.

The experimental loading of the supports with Pd was 0.77 wt.-%, that with Au 0.27 wt.-% (determined by means of ICP).

The shell thickness was 260 µm (statistical average).

The performance of the catalyst of the comparison example was determined analogously to Example 2 and shows a selectivity S(C$_2$H$_4$) of 92.1% and a space-time yield (determined by gas chromatography) of 410 g VAM/l catalyst/h with an oxygen conversion rate of 24.5%.

The invention claimed is:

1. Porous catalyst support consisting of a material comprising a natural sheet silicate comprising an acid-treated calcined bentonite containing ZrO$_2$ in particulate form dispersed throughout the material, wherein the ZrO$_2$ particles have a diameter of 0.5 to 20 µm and the proportion of acid-treated calcined bentonite in the catalyst support is greater than 80 mass-%.

2. Catalyst support according to claim 1, wherein the ZrO$_2$ is uniformly dispersed throughout the material.

3. Porous catalyst support, in the form of a shaped body, with an outer shell, wherein the catalyst support, at least in the area of the outer shell, comprises a matrix comprising a natural sheet silicate comprising an acid-treated calcined bentonite, in which zirconium oxide (ZrO$_2$) particles are uniformly dispersed in the matrix, wherein the ZrO$_2$ particles have a diameter of 0.5 to 20 µm and the proportion of acid-treated calcined bentonite in the catalyst support is greater than 80 mass-%.

4. Porous catalyst support consisting of a material comprising a natural sheet silicate comprising an acid-treated calcined bentonite containing ZrO$_2$ in particulate form dispersed throughout the material, wherein the ZrO$_2$ particles have a diameter of 0.5 to 20 µm and the proportion of acid-treated calcined bentonite in the catalyst support is greater than 80 mass-%, wherein the zirconium oxide particles are contained in the catalyst support at a proportion of greater than 5 but less than 20 mass-% relative to the mass of the catalyst support.

5. Catalyst support according to claim 1, wherein the solubility of the catalyst support in acetic acid is less than 8 wt.-%.

6. Catalyst support according to claim 1, wherein the catalyst support has an acidity of between 1 and 150 µval/g.

7. Catalyst support according to claim 1, wherein the catalyst support has an average pore diameter of from 8 to 30 nm.

8. Catalyst support according to claim 1, wherein the catalyst support has a surface area less than/equal to 145 m$^2$/g.

9. Catalyst support according to claim 1, wherein the catalyst support has a surface area of from 145 to 60 m$^2$/g.

10. Catalyst support according to claim 1, wherein the catalyst support has a hardness greater than/equal to 20 N.

11. Catalyst support according to claim 1, wherein the proportion of acid-treated calcined bentonite in the catalyst support is greater than/equal to 90 mass-% relative to the mass of the catalyst support.

12. Catalyst support according to claim 1, wherein the catalyst support has an integral BJH pore volume of between 0.25 and 0.7 ml/g.

13. Catalyst support according to claim 1, wherein at least 80% of the integral pore volume of the catalyst support is formed from mesopores and micropores.

14. Catalyst support according to claim 1, wherein the catalyst support has a bulk density of more than 0.3 g/ml.

15. Catalyst support according to claim 1, wherein the natural sheet silicate contained in the support has an SiO$_2$ content of at least 65 mass-%.

16. Catalyst support according to claim 1, wherein the natural sheet silicate contained in the support contains less than 10 mass-% Al$_2$O$_3$.

17. Catalyst support according to claim 1, wherein the catalyst support is formed as a sphere, cylinder, perforated cylinder, trilobe, ring, star or as a strand.

18. Catalyst support according to claim 1, wherein the catalyst support is formed as a sphere with a diameter greater than 2 mm.

19. Catalyst support according to claim 1, wherein the catalyst support is doped with at least one oxide of a metal selected from the group consisting of Hf, Ti, Nb, Ta, W, Mg, Re, Y and Fe.

20. Catalyst support according to claim 19, wherein the proportion of doping oxide in the catalyst support is between 1.0 and 20 mass-%.

* * * * *